(12) United States Patent
Somei et al.

(10) Patent No.: US 7,659,304 B2
(45) Date of Patent: Feb. 9, 2010

(54) TRYPTOPHAN DERIVATIVE AND APPLICATION THEREOF

(76) Inventors: Masanori Somei, 40-3, Ni, Sodanimachi, Hakusan-shi, Ishikawa 920-2101 (JP); Atsuhiko Hattori, 1-23-13, Sugano, Ichikawa-shi, Chiba 272-0824 (JP); Nobuo Suzuki, 2648, Ishisaka, Toyama-shi, Toyama 930-0892 (JP)

( * ) Notice: Subject to any disclaimer, the term of this patent is extended or adjusted under 35 U.S.C. 154(b) by 29 days.

(21) Appl. No.: 12/007,992

(22) Filed: Jan. 17, 2008

(65) Prior Publication Data

US 2009/0054511 A1 Feb. 26, 2009

Related U.S. Application Data (63) Continuation-in-part of application No. PCT/JP2006/312978, filed on Jun. 29, 2006.

(30) Foreign Application Priority Data

Jul. 20, 2005 (JP) ............................. 2005-209753

(51) Int. Cl.
*A61K 31/405* (2006.01)
*C07D 209/12* (2006.01)
(52) U.S. Cl. ..................... 514/419; 548/496
(58) Field of Classification Search .................. None
See application file for complete search history.

(56) References Cited

U.S. PATENT DOCUMENTS

| 6,787,550 | B1 | 9/2004 | Farina et al. |
| 2005/0209225 | A1 | 9/2005 | Lu et al. |

FOREIGN PATENT DOCUMENTS

| JP | 11-246406 A | 9/1999 |
| JP | 2003-503490 A | 1/2003 |
| JP | 2004-533993 A | 11/2004 |
| JP | 2005-289985 A | 10/2005 |
| WO | WO-2001/02388 A1 | 1/2001 |
| WO | WO-2002/60438 A1 | 8/2002 |
| WO | WO-2004/110983 A2 | 12/2004 |
| WO | WO-2005/084664 A1 | 9/2005 |

OTHER PUBLICATIONS

Hobar, Coburn, MD. "Prevention of Osteoporosis." eMedicineHealth: Practical Guide to Health. (2005). Accessed May 19, 2009. <http://www.emedicinehealth.com/prevention_of_osteoporosis/article_em.htm>.*

Namkung-Matthai, H. et al. "Osteoporosis Influences the Early Period of Fracture Healing in a Rat Osteoporotic Model." Bone. vol. 28, No. 1, Jan. 2001: 80-86.*
Patani et al. "Bioisosterism: A Rational Approach in Drug Design." Chem Rev. 1996, 96 (8), pp. 3147-3176.*
Schmidt and Weinbrenner. "Preparation of 2-Bromo-5-hydroxytryptophans." Synthesis (Jan. 1996): 28-30.*
Schmidt U., Synthesis, 1996, No. 1, pp. 28-30.
Suzuki N., Journal of Pineal Research, 2002, vol. 33, No. 4, pp. 253-258.
Roth J.A., The Journal of biological chemistry, 1999. vol. 274, No. 31, pp. 22041-22047.

\* cited by examiner

*Primary Examiner*—Rei-Tsang Shiao
*Assistant Examiner*—Alicia L Fierro
(74) *Attorney, Agent, or Firm*—Birch, Stewart, Kolasch & Birch, LLP (57) ABSTRACT

A compound represented by the following formula (I) or a salt thereof is provided:

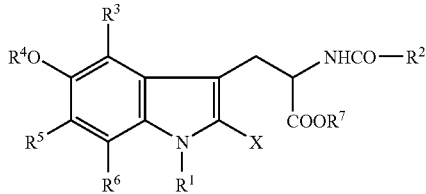

wherein X represents a halogen atom; $R^1$ represents a hydrogen atom, substituted or unsubstituted $C_{1-6}$ alkyl group, substituted or unsubstituted $C_{2-6}$ alkenyl group, substituted or unsubstituted $C_{2-6}$ alkynyl group, substituted or unsubstituted aromatic group, substituted or unsubstituted aralkyl group, substituted or unsubstituted acyl group, substituted or unsubstituted arylsulfonyl group, substituted or unsubstituted $C_{1-6}$ alkylsulfonyl group, substituted or unsubstituted $C_{2-7}$ alkoxycarbonyl group, or hydroxyl group; $R^2$ represents a substituted or unsubstituted $C_{1-21}$ alkyl group; $R^3$, $R^5$, and $R^6$ are the same or different and represent a hydrogen atom or halogen atom; $R^4$ represents a hydrogen atom or substituted or unsubstituted $C_{1-6}$ alkyl group; and $R^7$ represents a hydrogen atom or substituted or unsubstituted $C_{1-21}$ hydrocarbon group. Also provided is a therapeutic drug for osteoporosis and an osteoblast activator comprising the compound or a salt thereof.

6 Claims, 1 Drawing Sheet
(1 of 1 Drawing Sheet(s) Filed in Color)

TRYPTOPHAN DERIVATIVE AND APPLICATION THEREOF

CROSS REFERENCE TO RELATED APPLICATIONS

This application is a Continuation-In-Part of copending PCT International Application No. PCTJP2006/312978 filed on Jun. 29, 2006, which designated the United States and on which priority is claimed under 35 U.S.C. § 120, and also claims priority under 35 U.S.C. § 119 on Japanese Patent Application No. 2005-209753 filed in Japan on Jun. 20, 2005. The entire contents of both of these applications are hereby incorporated by reference.

TECHNICAL FIELD

The present invention relates to a tryptophan derivative and applications thereof. Particularly, the present invention relates to a therapeutic drug for osteoporosis and an osteoblast activator.

BACKGROUND ART

Osteoporosis is developed due to the disruption of the balance between the functions of osteoblasts responsible for bone formation and osteoclasts responsible for bone resorption. Compounds that activate osteoblasts and the other compounds that inhibit osteoclasts are considered to be effective for the treatment of osteoporosis. Estrogen may activate osteoblasts and inhibit osteoclasts and has been used in the treatment of osteoporosis. However, it also acts on cells other than bone, particularly, on reproductive organs. Therefore, there is concern about side effects such as increased risks of uterine cancer and breast cancer. Moreover, the Ministry of Health, Labour and Welfare issued safety information dated Jan. 29, 2004 alerting people that the long-term estrogen medication might increase a chance of the onset of breast cancer or dementia. Furthermore, the synthesis of estrogen is complicated and difficult because of its complex molecular structure.

Melatonin (N-acetyl-5-methoxytryptamine) having an indole skeleton has been reported to act in an inhibitory manner on both osteoblasts and osteoclasts (Non-Patent Document 1). However, there has been no report about the relationship between a tryptophan derivative and its effect on osteoblasts and osteoclasts.

Non-Patent Document 1: N. Suzuki and A. Hattori, J. Pineal Res., 33, 253-258 (2002)

DISCLOSURE OF THE INVENTION

An object of the present invention is to provide a pharmaceutically useful tryptophan derivative, particularly, a tryptophan derivative that activates osteoblasts, and to provide a therapeutic drug for osteoporosis and an osteoblast activator using this tryptophan derivative.

The present invention encompasses the following inventions:

(1) A compound represented by the following formula (I) or a salt thereof:

wherein X represents a halogen atom; $R^1$ represents a hydrogen atom, substituted or unsubstituted $C_{1-6}$ alkyl group, substituted or unsubstituted $C_{2-6}$ alkenyl group, substituted or unsubstituted $C_{2-6}$ alkynyl group, substituted or unsubstituted aromatic group, substituted or unsubstituted aralkyl group, substituted or unsubstituted acyl group, substituted or unsubstituted arylsulfonyl group, substituted or unsubstituted $C_{1-6}$ alkylsulfonyl group, substituted or unsubstituted $C_{2-7}$ alkoxycarbonyl group, or hydroxyl group; $R^2$ represents a substituted or unsubstituted $C_{1-21}$ alkyl group; $R^3$, $R^5$, and $R^6$ are the same or different and represent a hydrogen atom or halogen atom; $R^4$ represents a hydrogen atom or substituted or unsubstituted $C_{1-6}$ alkyl group; and $R^7$ represents a hydrogen atom or substituted or unsubstituted $C_{1-21}$ hydrocarbon group.

(2) The compound represented by the formula (I) described above or a salt thereof, wherein X is a bromine atom; $R^1$ is a hydrogen atom, substituted or unsubstituted $C_{1-6}$ alkyl group, substituted or unsubstituted $C_{2-6}$ alkenyl group, substituted or unsubstituted $C_{2-6}$ alkynyl group, substituted or unsubstituted aromatic group, substituted or unsubstituted aralkyl group, substituted or unsubstituted acyl group, substituted or unsubstituted arylsulfonyl group, substituted or unsubstituted $C_{1-6}$ alkylsulfonyl group, or substituted or unsubstituted $C_{2-7}$ alkoxycarbonyl group; $R^2$ is a methyl group; $R^3$, $R^5$, and $R^6$ are the same or different and are a hydrogen atom or bromine atom; $R^4$ is a methyl group; and $R^7$ is a $C_{1-6}$ alkyl group.

(3) A pharmaceutical composition comprising the compound according to (1) or (2) or a pharmaceutically acceptable salt thereof as an active ingredient.

(4) A therapeutic drug for osteoporosis comprising the compound according to (1) or (2) or a pharmaceutically acceptable salt thereof as an active ingredient.

(5) An osteoblast activator comprising the compound according to (1) or (2) or a salt thereof.

The present invention can provide a tryptophan derivative that activates osteoblasts and can provide a therapeutic drug for osteoporosis and an osteoblast activator using this tryptophan derivative. Moreover, the tryptophan derivative of the present invention can be synthesized more easily than estrogen and can be produced in large amounts.

BEST MODE FOR CARRYING OUT THE INVENTION

Hereinafter, the present invention will be described in detail.

In the present invention, examples of a $C_{1-6}$ alkyl group and a "$C_{1-6}$ alkyl group" in each substituent include a methyl group, ethyl group, propyl group, isopropyl group, butyl group, isobutyl group, sec-butyl group, tert-butyl group, pentyl group, isopentyl group, hexyl group, cyclopropyl group, cyclobutyl group, cyclopentyl group, and cyclohexyl group.

Examples of a $C_{1-21}$ alkyl group include a methyl group, ethyl group, propyl group, isopropyl group, butyl group, isobutyl group, sec-butyl group, tert-butyl group, pentyl group, isopentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, icosyl group, henicosyl group, cyclopropyl group, cyclobutyl group, cyclopentyl group, and cyclohexyl group.

A $C_{1-21}$ alkyl group represented by $R^2$ in the formula (I) is, preferably, a $C_{1-6}$ alkyl group, more preferably, a methyl group.

Examples of a $C_{2-6}$ alkenyl group include a vinyl group, 1-propenyl group, allyl group, 1-butenyl group, 2-butenyl group, pentenyl group, and hexenyl group.

Examples of a $C_{2-6}$ alkynyl group include an ethynyl group, 1-propynyl group, 2-propynyl (propargyl) group, 3-butynyl group, pentynyl group, and hexynyl group.

Examples of an aromatic group include: aromatic hydrocarbon groups such as a phenyl group, tolyl group, and naphthyl group; and aromatic heterocyclic groups such as a furyl group, thienyl group, pyrrolyl group, oxazolyl group, isoxazolyl group, thiazolyl group, isothiazolyl group, imidazolyl group, pyrazolyl group, pyridyl group, pyrimidinyl group, pyridazinyl group, pyrazinyl group, quinolyl group, and isoquinolyl group.

Examples of an aralkyl group include a benzyl group and phenethyl group.

Examples of a $C_{1-21}$ hydrocarbon group include: linear or branched $C_{1-21}$ alkyl groups such as a methyl group, ethyl group, propyl group, isopropyl group, butyl group, isobutyl group, sec-butyl group, tert-butyl group, pentyl group, isopentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, icosyl group, and henicosyl group; $C_{3-21}$ cycloalkyl groups such as a cyclopropyl group, cyclobutyl group, cyclopentyl group, cyclohexyl group, and cycloheptyl group; $C_{2-21}$ alkenyl groups such as a vinyl group, 1-propenyl group, allyl group, 1-butenyl group, 2-butenyl group, pentenyl group, hexenyl group, and oleyl group; $C_{2-21}$ alkynyl groups such as an ethynyl group, 1-propynyl group, 2-propynyl (propargyl) group, 3-butynyl group, pentynyl group, and hexynyl group; aromatic hydrocarbon groups such as a phenyl group, tolyl group, and naphthyl group; aralkyl groups such as a benzyl group and phenethyl group; bridged cyclic hydrocarbon groups such as an adamantyl group; spirocyclic hydrocarbon groups; and condensed ring hydrocarbon groups.

Examples of an acyl group include: $C_{1-6}$ aliphatic acyl groups such as a formyl group, acetyl group, propionyl group (propanoyl group), butyryl group (butanoyl group), valeryl group (pentanoyl group), and hexanoyl group; and aromatic acyl groups (aroyl groups) such as a benzoyl group and toluoyl group.

Examples of an arylsulfonyl group include: aromatic hydrocarbon-sulfonyl groups such as a phenylsulfonyl group (benzenesulfonyl group), p-toluenesulfonyl (tosyl) group, and naphthalenesulfonyl group; and aromatic heterocyclic sulfonyl groups such as a furansulfonyl group, thiophenesulfonyl group, pyrrolesulfonyl group, oxazolesulfonyl group, isoxazolesulfonyl group, thiazolesulfonyl group, isothiazolesulfonyl group, imidazolesulfonyl group, pyrazolesulfonyl group, pyridinesulfonyl group, pyrimidinesulfonyl group, pyridazinesulfonyl group, pyrazinesulfonyl group, quinolinesulfonyl group, and isoquinolinesulfonyl group.

Examples of a $C_{1-6}$ alkylsulfonyl group include a methanesulfonyl (mesyl) group and ethanesulfonyl group.

A $C_{2-7}$ alkoxycarbonyl group refers to a carbonyl group substituted by a $C_{1-6}$ alkoxy group. Examples thereof include a methoxycarbonyl group, ethoxycarbonyl group, propoxycarbonyl group, and tert-butoxycarbonyl group.

Examples of a halogen atom include a fluorine atom, chlorine atom, bromine atom, and iodine atom.

A $C_{1-6}$ alkyl group and $C_{1-21}$ alkyl group represented by $R^1$, $R^2$, or $R^4$, a $C_{2-6}$ alkenyl group, $C_{2-6}$ alkynyl group, $C_{1-6}$ alkylsulfonyl group, and $C_{2-7}$ alkoxycarbonyl group represented by $R^1$, and a $C_{1-21}$ hydrocarbon group represented by $R^7$ in the formula (I) may be substituted by one or more substituents selected from an aromatic group, acyl group, hydroxyl group, carboxy group, halogen atom, $C_{1-6}$ alkoxy group (e.g., a methoxy group, ethoxy group, and propoxy group), and so on.

An aromatic group, aralkyl group, acyl group, and arylsulfonyl group represented by $R^1$ in the formula (I) may be substituted by one or more substituents selected from a $C_{1-6}$ alkyl group, $C_{2-6}$ alkenyl group, $C_{2-6}$ alkynyl group, aromatic group, acyl group, hydroxyl group, carboxy group, halogen atom, $C_{1-6}$ alkoxy group (e.g., a methoxy group, ethoxy group, and propoxy group), and so on.

A salt of the compound represented by the formula (I) is, preferably, a pharmaceutically acceptable salt. Examples thereof include: salts with inorganic acids such as hydrochloric acid, sulfuric acid, phosphoric acid, hydrobromic acid, hydroiodic acid, nitric acid, pyrosulfuric acid, and metaphosphoric acid; and salts with organic acids such as citric acid, benzoic acid, acetic acid, propionic acid, fumaric acid, maleic acid, and sulfonic acid (e.g., methanesulfonic acid, p-toluenesulfonic acid, and naphthalenesulfonic acid). Alternatively, when the compound represented by the formula (I) has a phenolic hydroxyl group or carboxyl group, it can also be used in the form of an alkali metal salt such as a sodium salt and potassium salt.

Of compounds represented by the formula (I), a compound wherein $R^1$ is a hydrogen atom can be produced, for example, by halogenating a compound represented by the formula (I) wherein X is a hydrogen atom (e.g., N-acetyl-5-methoxytryptophan methyl ester). Alternatively, a compound represented by the formula (I) wherein $R^1$ is a hydroxyl group and X is a halogen atom can also be produced by halogenating a compound represented by the formula (I) wherein $R^1$ is a hydroxyl group and X is a hydrogen atom (e.g., N-acetyl-1-hydroxy-5-methoxytryptophan methyl ester).

Of compounds represented by the formula (I), a compound wherein $R^1$ is a substituted or unsubstituted $C_{1-6}$ alkyl group, substituted or unsubstituted $C_{2-6}$ alkenyl group, substituted or unsubstituted $C_{2-6}$ alkynyl group, substituted or unsubstituted aromatic group, substituted or unsubstituted aralkyl group, substituted or unsubstituted acyl group, substituted or unsubstituted arylsulfonyl group, or substituted or unsubstituted $C_{1-6}$ alkylsulfonyl group can be produced, for example, by reacting the thus-obtained compound represented by the formula (I) wherein $R^1$ is a hydrogen atom and X is a halogen atom with a compound represented by the formula: $R^1$—X (wherein $R^1$ represents a substituted or unsubstituted $C_{1-6}$ alkyl group, substituted or unsubstituted $C_{2-6}$ alkenyl group, substituted or unsubstituted $C_{2-6}$ alkynyl group, substituted or unsubstituted aromatic group, substituted or unsubstituted aralkyl group, substituted or unsubstituted acyl group, substituted or unsubstituted arylsulfonyl group, or substituted or unsubstituted $C_{1-6}$ alkylsulfonyl group; and X represents a halogen atom) in the presence of a basic catalyst in an organic solvent such as N,N-dimethylformamide.

Of compounds represented by the formula (I), a compound wherein $R^1$ is a substituted or unsubstituted $C_{2-7}$ alkoxycarbonyl group can be produced, for example, by reacting the compound represented by the formula (I) wherein $R^1$ is a hydrogen atom and X is a halogen atom with a compound represented by the formula: $(R^1)_2O$ (wherein $R^1$ represents a substituted or unsubstituted $C_{2-7}$ alkoxycarbonyl group) in the presence of a basic catalyst in an organic solvent such as chloroform.

Of compounds represented by the formula (I), a compound wherein $R^1$ is a hydroxyl group can be produced, for example, by treating a compound represented by the formula (I) wherein $R^1$ and X are a hydrogen atom with hydrogen peroxide and sodium tungstate, followed by halogenation.

Of compounds represented by the formula (I), a compound wherein $R^4$ is a hydrogen atom can be produced, for example, by halogenating (e.g., treating with a brominating agent such as bromine or N-bromosuccinimide using acetic acid, chloroform, or the like as a solvent) a compound represented by the formula (I) wherein X and $R^4$ are a hydrogen atom (e.g., the compound wherein $R^1$, $R^3$, $R^5$, and $R^6$ are a hydrogen atom).

For acyl group (—CO—$R^2$) conversion, the compound represented by the formula (I) can be hydrolyzed in the presence of a basic catalyst for the elimination of the acyl group and then treated with an acid anhydride ($R^{2'}$CO—O—CO$R^{2'}$) or the like, followed by the introduction of another acyl group. In this procedure, the deacylated product as an intermediate is generally likely to be oxidized in air. Therefore, it is preferred that the deacylated product should be used in the subsequent acylation step without purification.

Of compounds represented by the formula (I), a compound wherein $R^7$ is a hydrogen atom can be produced, for example, by hydrolyzing a compound wherein $R^7$ is a methyl group by heating with a sodium hydroxide aqueous solution.

The product thus obtained may be purified by an approach usually used, for example, column chromatography using silica gel or the like as a carrier or a recrystallization method using methanol, ethanol, chloroform, dimethyl sulfoxide, water, or the like. Examples of an elution solvent in column chromatography include methanol, ethanol, chloroform, acetone, hexane, dichloromethane, ethyl acetate, and mixed solvents thereof.

The compound represented by the formula (I) and the salt thereof (hereinafter, referred to as a "tryptophan derivative (I)") have the effect of activating osteoblasts and are useful as a pharmaceutical composition for preventing or treating various diseases related to bone, for example, osteoporosis, or as an osteoblast activator in various fields, for example, regenerative medicine, dental fields, the growth of fishes, and meat or egg production by the healthy growth of livestock. Moreover, the tryptophan derivative (I) has a radical scavenger effect and is also useful as a pharmaceutical composition for preventing or treating insomnia or lifestyle-related disease. Furthermore, the tryptophan derivative of the present invention can also be expected to have potential use as a pharmaceutical drug other than those described above, for example, a vasodilator, hypotensive agent, amino acid supplement, anticancer agent, and antiplatelet agent.

A therapeutic drug for osteoporosis comprising the tryptophan derivative of the present invention as an active ingredient can be used in combination with other therapeutic drugs for osteoporosis, for example, a calcium preparation, vitamin D-based preparation, hormone-based preparation, calcitonin-based preparation, bisphosphonate preparation, and ipriflavone preparation. In this case, a dose described below can be increased or decreased appropriately as required.

Hereinafter, the dose of the tryptophan derivative (I) and the production of a preparation thereof will be described.

The tryptophan derivative (I) can be administered to animals and humans either directly or together with a pharmaceutical carrier commonly used. Its dosage form is not particularly limited and is appropriately selected as required for use. Examples thereof include: oral preparations such as tablets, capsules, granules, fine granules, powders, sustained-release preparations, suspensions, emulsions, syrups, and elixirs; and parenteral preparations such as injections, suppositories, liniments, and adhesive preparations.

The oral preparations are produced according to a standard method using, for example, starch, lactose, sucrose, mannitol, carboxymethylcellulose, corn starch, and inorganic salts.

In addition to the excipients described above, binders, disintegrators, surfactants, lubricants, fluidity promoters, corrigents, coloring agents, flavors, and so on can be used appropriately in this kind of preparation.

Examples of the binders include starch, dextrin, powdered acacia, gelatin, hydroxypropyl starch, methylcellulose, carboxymethylcellulose sodium, hydroxypropylcellulose, crystalline cellulose, ethylcellulose, polyvinyl pyrrolidone, and macrogol.

Examples of the disintegrators include starch, hydroxypropyl starch, carboxymethylcellulose sodium, carboxymethylcellulose calcium, carboxymethylcellulose, and low-substituted hydroxypropylcellulose.

Examples of the surfactants include sodium lauryl sulfate, soybean lecithin, sucrose fatty acid ester, and polysorbate 80.

Examples of the lubricants include talc, waxes, hydrogenated plant oils, sucrose fatty acid ester, magnesium stearate, calcium stearate, aluminum stearate, and polyethylene glycol.

Examples of the fluidity promoters include light anhydrous silicic acid, dried aluminum hydroxide gel, synthetic aluminum silicate, and magnesium silicate.

The injections are produced according to a standard method, and distilled water for injection, a saline, a glucose aqueous solution, olive oil, sesame oil, peanut oil, soybean oil, corn oil, propylene glycol, polyethylene glycol, or the like can generally be used as a diluent. If necessary, a germicide, antiseptic, and stabilizer may further be added thereto. Moreover, in light of stability, the injections are charged into vials or the like and then frozen, followed by removal of water by a usual freeze-drying technique, and a liquid preparation can be reprepared from the freeze-dried product immediately before use. If necessary, tonicity agents, stabilizers, antiseptics, soothing agents, and so on may be added appropriately.

Examples of the other parenteral preparations include liquid preparations for external use, liniments such as ointments, adhesive preparations, and suppositories for intrarectal administration. They are produced according to a standard method.

The preparation of the present invention may be administered at one to several doses per day to one to several doses per week to month, though the dose differs depending on its dosage form, administration route, and so on.

To exert the intended effect as an oral preparation, an appropriate dose of the preparation in adult is usually 1 to 200 mg in terms of the weight of the tryptophan derivative (I) taken at several doses per day, though the dose differs depending on the age and body weight of a patient and the extent of the disease.

To exert the intended effect as a parenteral preparation, an appropriate dose of the preparation in adult is usually 1 to 50 mg per day in terms of the weight of the tryptophan derivative (I) administered through intravenous injection, intravenous drips, hypodermic injection, or intramuscular injection, though the dose differs depending on the age and body weight of a patient and the extent of the disease.

The patent or application file contains at least one drawing executed in color. Copies of this patent or patent application publication with color drawing(s) will be provided by the office upon request and payment of the necessary fee.

This description includes part or all of the contents as disclosed in the description of Japanese Patent Application No. 2005-209753, which is a priority document of the present application.

EXAMPLES

Hereinafter, the present invention will be described more specifically with reference to Examples. However, the scope of the present invention is not intended to be limited to these Examples.

Example 1

Synthesis of (S)-(+)-N-acetyl-2,6-dibromo-5-methoxytryptophan methyl ester (2), (S) -(+)-N-acetyl-2,4,7-tribromo-5-methoxytryptophan methyl ester (3), and (S)-(+)-N-acetyl-2,4,6-tribromo-5-methoxytryptophan methyl ester (4) from (S)-(+)-N-acetyl-5-methoxytryptophan methyl ester (1)

A solution containing 56.6 mg (0.20 mmol) of (S)-(+)-N-acetyl-5-methoxytryptophan methyl ester (1) (which was synthesized according to a method described in M. Somei and Y. Fukui, Heterocycles, 36, 1859 (1993) and can also be obtained from commercially available products, albeit expensive) dissolved in 4.5 mL of acetic acid was charged with 1.0 mL (0.59 mmol) of bromine solution separately prepared by dissolving 458.0 mg of bromine and 41.8 mg of sodium acetate in 5.0 mL of acetic acid. The mixture was stirred at room temperature for 30 minutes. The reaction solution was charged with 1.0 mL of 10% hypo aqueous solution and with a chloroform-methanol (95:5, v/v) mixed solvent. Then, the whole solution was rendered alkaline by the addition of a 40% sodium hydroxide aqueous solution. Subsequently, the solution was subjected to extraction with a chloroform-methanol (95:5, v/v) mixed solvent. The organic phase was washed with a saturated saline and dried over anhydrous sodium sulfate. Then, the solvent was distilled off under reduced pressure to obtain yellow solid. Column chromatography using silica gel as a carrier and a chloroform-methanol (99.5:0.5, v/v) mixed solvent as an elution solvent was performed to obtain 28.4 mg of mixture of (S)-(+)-N-acetyl-2,6-dibromo-5-methoxytryptophan methyl ester (2) and (S)-(+)-N-acetyl-2,4,7-tribromo-5-methoxytryptophan methyl ester (3) difficult to separate, and subsequently, 53.7 mg (52%) of (S)-(+)-N-acetyl-2,4,6-tribromo-5-methoxytryptophan methyl ester (4), in the order of elution.

[Compound (4)]

mp 198-199° C. (colorless granular crystals, recrystallized from ethyl acetate).

IR (KBr): 3307, 1730, 1647, 1556, 1300, 1232, 1028 cm$^{-1}$.

$^1$H-NMR (CDCl$_3$) δ: 1.88 (3H, s), 3.29 (1H, dd, J=9.8, 14.6 Hz), 3.58 (1H, dd, J=5.2, 14.6 Hz), 3.77 (3H, s), 3.88 (3H, s), 5.01 (1H, ddd, J=5.2, 8.6, 9.8 Hz, changed to dd, J=5.2, 9.8 Hz by addition of D$_2$O), 6.17 (1H, br d, J=8.6 Hz, disappeared by addition of D$_2$O), 7.37 (1H, s), 8.70 (1H, br s, disappeared by addition of D$_2$O).

Mass Spectrometry m/z: 530 (M$^+$), 528 (M$^+$), 526 (M$^+$), 524 (M$^+$).

Anal. Calcd for: C$_{15}$H$_{15}$Br$_3$N$_2$O$_4$: C, 34.19; H, 2.87; N, 5.32. Found: C, 34.24; H, 2.89; N, 5.18.

Optical Rotation [α]$_D^{26}$+14.8° (DMSO, c=0.200). [α]$_D^{27}$+1.47° (MeOH, c=0.204).

[α]$_D^{28}$+4.4° (CHCl$_3$, c=0.203).

Example 2

Synthesis of (S)-(+)-N-acetyl-2,4,6-tribromo-1-t-butoxycarbonyl-5-methoxytryptophan methyl ester (5) from (S)-(+)-N-acetyl-2,4,6-tribromo-5-methoxytryptophan methyl ester (4)

4

5

A solution containing 49.3 mg (0.09 mmol) of (S)-(+)-N-acetyl-2,4,6-tribromo-5-methoxytryptophan methyl ester (4) dissolved in 10.0 mL of chloroform was charged with a solution containing 3.4 mg (0.03 mmol) of dimethylaminopyridine and 30.6 mg (0.14 mmol) of di-t-butyl dicarbonate dissolved in 1.0 mL of chloroform. The mixture was stirred at room temperature for 30 minutes. The reaction solution was distilled off under reduced pressure to obtain yellow oil. Purification by column chromatography using silica gel as a carrier and a chloroform-methanol (99:1, v/v) mixed solvent as an elution solvent was performed to obtain the substance of interest (5) at a yield of 57.5 mg (98%).

mp 126-128° C. (colorless needle-like crystals, recrystallized from chloroform-hexane).

IR (KBr): 3435, 1759, 1732, 1651, 1396, 1275, 1159, 1111 cm$^{-1}$.

$^1$H-NMR (CDCl$_3$) δ: 1.69 (9H, s), 1.89 (3H, s), 3.38 (1H, dd, J=10.1, 14.3 Hz), 3.65 (1H, dd, J=5.2, 14.3 Hz), 3.75 (3H, s), 3.90 (3H, s), 5.07 (1H, ddd, J=5.2, 8.5, 10.1 Hz, changed to dd, J=5.2, 10.1 Hz by addition of D$_2$O), 6.14 (1H, br d, J=8.5 Hz, disappeared by addition of D$_2$O), 8.39 (1H, s).

Mass Spectrometry m/z: 630 (M$^+$), 628 (M$^+$), 626 (M$^+$), 624 (M$^+$).

Anal. Calcd for: C$_{20}$H$_{23}$Br$_3$N$_2$O$_6$: C, 38.30; H, 3.70; N, 4.47. Found: C, 38.18; H, 3.74; N, 4.45.

Optical Rotation [α]$_D^{24}$+3.3° (CHCl$_3$, c=0.200).

Example 3

Synthesis of (S)-(+)-N-acetyl-1-allyl-2,4,6-tribromo-5-methoxytryptophan methyl ester (6) from (S)-(+)-N-acetyl-2,4,6-tribromo-5-methoxytryptophan methyl ester (4)

4

6

A solution containing 39.8 mg (0.08 mmol) of (S)-(+)-N-acetyl-2,4,6-tribromo-5-methoxytryptophan methyl ester (4) dissolved in 2.5 mL of N,N-dimethylformamide was charged with 36.5 mg (0.26 mmol) of potassium carbonate and subsequently with 0.13 mL (d=1.398, 1.51 mmol) of allyl bromide. The mixture was stirred at room temperature for 30 minutes. The reaction solution was charged with water and subjected to extraction with ethyl acetate. The organic phase was washed with a saturated saline and dried over anhydrous sodium sulfate. Then, the solvent was distilled off under reduced pressure to obtain yellow oil. Purification by column chromatography using silica gel as a carrier and chloroform as an elution solvent was performed to obtain the substance of interest (6) at a yield of 42.4 mg (99%).

mp 191-192° C. (colorless needle-like crystals, recrystallized from ethyl acetate).

IR (KBr): 3303, 1732, 1645, 1547, 1228, 1016 cm$^{-1}$.

$^1$H-NMR (CDCl$_3$) δ: 1.86 (3H, s), 3.34 (1H, dd, J=9.8, 14.7 Hz), 3.62 (1H, dd, J=5.4, 14.7 Hz), 3.74 (3H, s), 3.89 (3H, s), 4.75 (2H, m), 4.83 (1H, d, J=17.1 Hz), 5.01 (1H, ddd, J=5.4, 8.7, 9.8 Hz, changed to dd, J=5.4, 9.8 Hz by addition of D$_2$O), 5.19 (1H, d, J=10.3 Hz), 5.86 (1H, tdd, J=4.8, 10.3, 17.1 Hz), 6.12 (1H, br d, J=8.7 Hz, disappeared by addition of D$_2$O), 7.41 (1H, s).

Mass Spectrometry m/z: 570 (M$^+$), 568 (M$^+$), 566 (M$^+$), 564 (M$^+$).

Anal. Calcd for: C$_{18}$H$_{19}$Br$_3$N$_2$O$_4$: C, 38.12; H, 3.38; N, 4.94. Found: C, 37.97; H, 3.43; N, 4.86.

Optical Rotation [α]$_D^{26}$+13.8° (CHCl$_3$, c=0.203).

Example 4

Synthesis of (S)-(+)-N-acetyl-2,4,6-tribromo-5-methoxy-1-propargyltryptophan methyl ester (7) from (S)-(+)-N-acetyl-2,4,6-tribromo-5-methoxytryptophan methyl ester (4)

A solution containing 23.6 mg (0.04 mmol) of (S)-(+)-N-acetyl-2,4,6-tribromo-5-methoxytryptophan methyl ester (4) dissolved in 2.0 mL of N,N-dimethylformamide was charged with 21.6 mg (0.16 mmol) of potassium carbonate and subsequently with 0.08 mL (d=1.335, 0.9 mmol) of propargyl bromide. The mixture was stirred at room temperature for 30 minutes. The reaction solution was charged with water and subjected to extraction with ethyl acetate. The organic phase was washed with a saturated saline and dried over anhydrous sodium sulfate. Then, the solvent was distilled off under reduced pressure to obtain pink oil. Purification by column chromatography using silica gel as a carrier and chloroform as an elution solvent was performed to obtain the substance of interest (7) at a yield of 23.9 mg (94%).

mp 284-285° C. (decomposition point, measurement with a sealed tube, colorless needle-like crystals, recrystallized from chloroform-methanol).

IR (KBr): 3284, 3224, 2114, 1724, 1647, 1552, 1230, 1016 cm$^{-1}$.

$^1$H-NMR (DMSO-d$_6$) δ: 1.82 (3H, s), 3.28 (1H, dd, J=7.1, 14.9 Hz), 3.33 (1H, dd, J=8.7, 14.9 Hz), 3.33 (1H, t, J=2.4 Hz), 3.48 (3H, s), 3.80 (3H, s), 4.47 (1H, ddd, J=7.1, 7.1, 8.7 Hz, changed to dd, J=7.1, 8.7 Hz by addition of D$_2$O), 5.13 (2H, dt, J=2.4, 4.2 Hz), 8.02 (1H, s), 8.44 (1H, br d, J=7.1 Hz, disappeared by addition of D$_2$O).

Mass Spectrometry m/z: 568 (M$^+$), 566 (M$^+$), 564 (M$^+$), 562 (M$^+$).

Anal. Calcd for: C$_{18}$H$_{17}$Br$_3$N$_2$O$_4$: C, 38.26; H, 3.03; N, 4.96. Found: C, 38.11; H, 3.12; N, 4.83.

Optical Rotation [α]$_D^{24}$+7.7° (DMSO, c=0.202).

Example 5

Synthesis of (S)-(+)-N-acetyl-1-benzyl-2,4,6-tribromo-5-methoxytryptophan methyl ester (8) from (S)-(+)-N-acetyl-2,4,6-tribromo-5-methoxytryptophan methyl ester (4)

A solution containing 19.6 mg (0.04 mmol) of (S)-(+)-N-acetyl-2,4,6-tribromo-5-methoxytryptophan methyl ester (4) dissolved in 1.5 mL of N,N-dimethylformamide was charged with 18.0 mg (0.13 mmol) of potassium carbonate and subsequently with 0.09 mL (d =1.44,0.7 mmol) of benzyl bromide. The mixture was stirred at room temperature for 30 minutes. The reaction solution was charged with water and subjected to extraction with an ethyl acetate-methanol (95:5, v/v) mixed solvent. The organic phase was washed with a saturated saline and dried over anhydrous sodium sulfate. Then, the solvent was distilled off under reduced pressure to obtain yellow oil. Thin-layer chromatography using silica gel as a carrier and a chloroform-methanol (99:1, v/v) mixed solvent as a developing solvent was performed. A band having an Rf value of 0.18 to 0.29 was extracted with a chloroform-methanol (95:5, v/v) mixed solvent to obtain the substance of interest (8) at a yield of 22.0 mg (96%).

mp 226-227° C. (colorless needle-like crystals, recrystallized from methanol).

IR (KBr): 3298, 1732, 1643, 1550, 1414, 1230, 1018 cm$^{-1}$.

$^1$H-NMR (DMSO-d$_6$) δ: 1.80 (3H, s), 3.28 (1H, dd, J=7.1, 14.4 Hz), 3.40 (1H, dd, J=8.5, 14.7 Hz, appeared by addition of D$_2$O), 3.47 (3H, s), 3.79 (3H, s), 4.55 (1H, ddd, J=7.1, 7.1, 8.5 Hz, changed to dd, J=7.1, 8.5 Hz by addition of D$_2$O), 5.53 (2H, s), 6.96 (2H, d, J=7.1 Hz), 7.25 (1H, t, J=7.1 Hz), 7.31 (2H, t, J=7.1 Hz), 7.90 (1H, s) 8.45 (1H, d, J=7.1 Hz, disappeared by addition of D$_2$O).

Mass Spectrometry m/z: 620 (M$^+$), 618 (M$^+$), 616 (M$^+$), 614 (M$^+$).

Anal. Calcd for: C$_{22}$H$_{21}$Br$_3$N$_2$O$_4$: C, 42.82; H, 3.43; N, 4.54. Found: C, 42.69; H, 3.47; N, 4.56.

Optical Rotation [α]$_D^{24}$+8.3° (CHCl$_3$, c=0.204).

Example 6

Synthesis of (S)-(+)-N-acetyl-2,6-dibromo-1-t-butoxycarbonyl-5-methoxytryptophan methyl ester (9) from mixture of (S)-(+)-N-acetyl-2,6-dibromo-5-methoxytryptophan methyl ester (2) and (S)-(+)-N-acetyl-2,4,7-tribromo-5-methoxytryptophan methyl ester (3) and separation of compound (3)

The mixture was stirred at room temperature for 10 hours. The reaction solution was distilled off under reduced pressure to obtain yellow oil. Silica gel column chromatography using silica gel as a carrier and a chloroform-methanol (99:1, v/v) mixed solvent as an elution solvent was performed to obtain 39.0 mg of compound (9) and 62.0 mg of compound (3) in the order of elution.

[Compound (3)]

mp 218-220° C. (colorless prism crystals, recrystallized from chloroform-hexane).

IR (KBr): 3435, 3303, 1728, 1653, 1552 cm$^{-1}$.

$^1$H-NMR (CDCl$_3$) δ: 1.87 (3H, s), 3.31 (1H, dd, J=10.0, 14.6 Hz), 3.58 (1H, dd, J=5.1, 14.6 Hz), 3.75 (3H, s), 3.91 (3H, s), 5.00 (1H, ddd, J=5.1, 8.5, 10.0 Hz, changed to dd, J=5.1, 10.0 Hz by addition of D$_2$O), 6.12 (1H, br d, J=8.5 Hz, disappeared by addition of D$_2$O), 7.05 (1H, s), 8.31 (1H, br s, disappeared by addition of D$_2$O).

Mass Spectrometry m/z: 530 (M$^+$), 528 (M$^+$), 526 (M$^+$), 524 (M$^+$).

A solution containing 93.3 mg of the mixture of the compounds (2) and (3) difficult to separate (1:2 abundance ratio from NMR) dissolved in 10.0 mL of chloroform was charged with a solution containing 9.6 mg (0.08 mmol, 0.5 equivalents assuming that the whole mixture was in a tribromo form) of dimethylaminopyridine and 68.9 mg (0.31 mmol, 2.0 equivalents assuming that the whole mixture was in a tribromo form) of di-t-butyl dicarbonate dissolved in 1.0 mL of chloroform.

Anal. Calcd for: C$_{15}$H$_{15}$Br$_3$N$_2$O$_4$: C, 34.19; H, 2.87; N, 5.32. Found: C, 34.00; H, 2.91; N, 5.22.

Optical Rotation [α]$_D^{24+5.1°}$ (CHCl$_3$, c=0.207).

[Compound (9)]

colorless oil

IR (film): 3286, 2981, 1743, 1735, 1654 cm$^{-1}$.

$^1$H-NMR (CDCl$_3$) δ: 1.70 (9H, s), 1.99 (3H, s), 3.21 (1H, dd, J=7.6, 15.0 Hz), 3.24 (1H, dd, J=5.7, 15.0 Hz), 3.69 (3H, s), 3.97 (3H, s), 4.85 (1H, dt, J=5.7, 7.6 Hz, changed to dd, J=5.7, 7.6 Hz by addition of $D_2O$), 6.15 (1H, br d, J=7.6 Hz, disappeared by addition of $D_2O$), 7.17 (1H, s), 8.32 (1H, s).

High Resolution Mass Spectrometry m/z: Calcd for $C_{20}H_{24}Br_2N_2O_6$: 549.9960 ($M^+$), 547.9981 ($M^+$), 546.0011 ($M^+$). Found: 549.9932, 547.9963, 546.0003.

Optical Rotation $[\alpha]_D^{24}$ +12.9° ($CHCl_3$, c=0.210).

Example 7

Synthesis of (S)-(+)-N-acetyl-2,6-dibromo-5-methoxytryptophan methyl ester (2) from (S)-(+)-N-acetyl-2,6-dibromo-1-t-butoxycarbonyl-5-methoxytryptophan methyl ester (9)

To a solution containing 18.3 mg (0.03 mmol) of (S)-(+)-N-acetyl-2,6-dibromo-1-t-butoxycarbonyl-5-methoxytryptophan methyl ester (9) dissolved in 3.2 mL of chloroform, 0.8 mL of trifluoroacetic acid was added under ice cooling to prepare a 10% solution. Furthermore, the solution was stirred at room temperature for 12 hours. The reaction solution was charged with chloroform. The organic phase was washed with saturated sodium bicarbonate water. The resulting phase was further washed with a saturated saline and dried over anhydrous sodium sulfate. Then, the solvent was distilled off under reduced pressure to obtain colorless oil. Column chromatography using silica gel as a carrier and a chloroform-methanol (99:1, v/v) mixed solvent as an elution solvent was performed to obtain 10.3 mg (70%) of compound (2).

mp 174-175° C. (colorless prism crystals, recrystallized from methanol-water).

IR (KBr): 3363, 1745, 1716, 1660, 1647 $cm^{-1}$. IR ($CHCl_3$): 1739, 1674 $cm^{-1}$.

$^1$H-NMR ($CDCl_3$) δ: 1.98 (3H, s), 3.21 (1H, dd, J=4.6, 14.0 Hz), 3.24 (1H, dd, J=4.6, 14.0 Hz), 3.70 (3H, s), 3.93 (3H, s), 4.90 (1H, dt, J=7.6, 4.6 Hz, changed to t, J=4.6 Hz by addition of $D_2O$), 6.05 (1H, br d, J=7.6 Hz, disappeared by addition of $D_2O$), 7.07 (1H, s), 7.48 (1H, s), 8.01 (1H, br, disappeared by addition of $D_2O$).

Mass Spectrometry m/z: 450 ($M^+$), 448 ($M^+$), 446 ($M^+$).

Anal. Calcd for: $C_{15}H_{16}Br_2N_2O_4$: C, 40.20; H, 3.60; N, 6.25. Found: C, 40.27; H, 3.71; N, 6.17.

Optical Rotation $[\alpha]_D^{27}$ +12.0° (MeOH, c=0.217).

Example 8

Test on Influence of Tryptophan Derivative on Bone Cells

The influence of the tryptophan derivatives on bone cells was tested according to a method described in N. Suzuki and A. Hattori, J. Pineal Res., 33, 253-258 (2002).

Required pieces of scales were ablated from female goldfish (body weight: around 30 g) under anesthesia with MS222 (ethyl 3-aminobenzoate, methane sulfonic acid salt) (Aldrich). The scales were washed twice with an Eagle's minimum essential medium (Dainippon Pharmaceutical Co., Ltd.) containing 1% antibiotic (penicillin-streptomycin mixture). The same medium was added at 1 ml/well to a 24-well plate. The scales were added at several pieces (usually eight)/well thereto. Each tryptophan derivative was added at a concentration of $10^{-6}$ M to each well. Subsequently, these scales were cultured at 25° C. for 6 hours. A tryptophan derivative-free group (control) was also prepared to compare the effects on bone cells. In this test, two groups, one for osteoclasts and the other for osteoblasts, were used for the tryptophan derivatives and compared them with the control. To ensure the obtained results, the duplicate test was performed. Thus, in the 24-well plate, 6 tryptophan derivatives can be examined.

After culture, the medium was removed. The scales were fixed by the addition of 0.05 M cacodylic acid buffer (pH 7.4) containing 10% formalin. These scales were stored in 0.05 M cacodylic acid buffer at 4° C. until enzyme activity measurement.

(1) Influence on Osteoclasts: Tartrate-Resistant Acid Phosphatase (TRAP) Activity Measurement The scales treated by fixation were moved and weighed. After measurement, the scales were put into a 96-well microplate. To each well, 2001 of 100 mM acetate buffer (pH 5.3) containing 20 mM tartrate and 10 mM para-nitrophenol phosphate (substrate) was added. Reaction was performed at 25° C. for 20 minutes and subsequently terminated by the addition of a 3 M sodium hydroxide aqueous solution (50±1). Then, 1501 of the solution after the completion of reaction was transferred to another microplate. The amount of para-nitrophenol (p-NP) produced by TRAP was measured with a spectrophotometer (405 nm). The osteoclast activity was indicated as the amount of p-NP produced by the decomposition of para-nitrophenol phosphate per g of scale per minute.

The result is shown in Table 1.

TABLE 1

TRAP activity

| Compound No. | $R^1$ | $R^3$ | $R^5$ | $R^6$ | Concentration (M) | Amount of para-nitrophenol produced (mean ± standard error) (nmol/g of scale/min) |
|---|---|---|---|---|---|---|
| 4 | H | Br | Br | H | $10^{-6}$ | 0.699 ± 0.064 |
| 5 | Boc | Br | Br | H | $10^{-6}$ | 0.747 ± 0.063 |
| 6 | $CH_2$=CH—$CH_2$— | Br | Br | H | $10^{-6}$ | 0.882 ± 0.106 |
| 7 | CH≡C—$CH_2$— | Br | Br | H | $10^{-6}$ | 0.838 ± 0.056 |
| 8 | benzyl | Br | Br | H | $10^{-6}$ | 0.829 ± 0.047 |
| Melatonin | | | | | $10^{-6}$ | 0.467 ± 0.052*** |
| Control (free from tryptophan derivative) | | | | | | 0.700 ± 0.041 |

***$p < 0.001$ (2) Influence on Osteoblasts: Alkaline Phosphatase (ALP) Activity Measurement The scales treated by fixation were moved and weighed. After measurement, the scales were put into a 96-well microplate. To each well, 200l of 100 mM tris-HCl buffer (pH 9.5) containing 10 mM para-nitrophenol phosphate (substrate), 1 mM magnesium chloride, and 0.1 mM zinc chloride was added. Reaction was performed at 25° C. for 15 minutes and terminated by the addition of a 3 M sodium hydroxide aqueous solution (50 μl). Then, 150 μl of the solution after the completion of reaction was transferred to another microplate. The amount of p-NP produced by ALP was measured with a spectrophotometer (405 nm) to determine the activity.

The result is shown in Table 2.

TABLE 2

ALP activity

| Compound No. | $R^1$ | $R^3$ | $R^5$ | $R^6$ | Concentration (M) | Amount of para-nitrophenol produced (mean ± standard error) (nmol/g of scale/min) |
|---|---|---|---|---|---|---|
| 4 | H | Br | Br | H | $10^{-6}$ | 2.62 ± 0.20*** |
| 5 | Boc | Br | Br | H | $10^{-6}$ | 2.48 ± 0.42* |
| 6 | $CH_2$=CH—$CH_2$— | Br | Br | H | $10^{-6}$ | 2.39 ± 0.40* |
| 7 | CH≡C—$CH_2$— | Br | Br | H | $10^{-6}$ | 2.50 ± 0.51 |
| 8 | benzyl | Br | Br | H | $10^{-6}$ | 1.17 ± 0.32 |
| Melatonin | | | | | $10^{-6}$ | 1.06 ± 0.17* |
| Control (free from tryptophan derivative) | | | | | | 1.37 ± 0.18 |

*$p < 0.05$
***$p < 0.001$

Tables 1 and 2 show that melatonin acts in an inhibitory manner on both osteoclasts and osteoblasts, whereas the tryptophan derivatives of the present invention have the effect of activating osteoblasts. This result demonstrated that the tryptophan derivative of the present invention can serve as an excellent therapeutic drug for osteoporosis.

Example 9

Evaluation Test on Effect of Tryptophan Derivative on Bone Metabolism of Ovariectomized Model Rat A. Material And Method 1. Test Substance and Solvent A test substance was the compound No. 4 ((S)-(+)-N-acetyl-2,4,6-tribromo-5-methoxytryptophan methyl ester), which was a white powder having a molecular weight of 527, and was stored at room temperature. Commercially available dimethyl sulfoxide (DMSO, Wako Pure Chemical Industries, Ltd.) was purchased as a solvent and stored at room temperature.

2. Method for Preparing Test Substance

The solution of the test substance was administered in a volume of 100 μL/rat in consideration of the toxicity of the solvent. For a dose of 0.17 mg of the test substance (compound No. 4)/rat, 86.6 mg of the test substance was weighed and dissolved in 50.9 mL of the solvent (0.17 mg/0.1 mL).

3. Animal Used and Raising Conditions

Five-week-old female SPF SD (Crl:SD) rats were obtained from Charles River Laboratories Japan, Inc. After seven-day acclimation and quarantine, 6-week-old ovariectomized models were prepared. Administration was performed from the day following model preparation.

The animals were raised in the rat/mouse room of a test laboratory set to a temperature of 24±3° C., a humidity of 50±20%, the number of ventilations of approximately 10 to 20 times/hour, a lighting time of 12 hours/day (8:00 light on, 20:00 light off), and an illuminance of 150 to 300 Lux.

4. Administration Method

The test substance was administered once a day for 6 weeks by gavage administration to the rats without anesthesia under non-fasting by use of a feeding needle made of a metal and a syringe barrel. In this context, 1 week is defined as 7 days, and the day following ovariectomy when the administration was initiated is defined as Day 1. The amount of the solution administered was set to 0.1 mL/rat.

(Constitution of Group)

Groups described below were established and subjected to each treatment.

| Group name | Treatment/ feed | Substance administered | Dose (mg/rat) | Administration time | The number of doses (dose/week) | Administration period (day) | The number of animals |
|---|---|---|---|---|---|---|---|
| Group 1 | OVX/CRF-1 | Solvent | 0 | Daytime | 7 | 42 | 3 |
| Group 2 | OVX/CRF-1 | Test substance | 0.17 | Daytime | 7 | 42 | 3 |

(Bone Density Measurement)

The bone densities of the left femurs were measured using a peripheral bone density measurement apparatus PQCT (abbreviation of peripheral Quantitative Computed Tomography, XCT-Research SA+, Stratec). For cancellous bone parameter measurement, the metaphyseal region was sliced at a distance of 3 mm from the distal growth cartilage. Alternatively, for cortical bone parameter measurement, the diaphyseal region was sliced at a distance of 13 mm therefrom. The measurement parameters were a bone density (total density and cancellous bone), an area (total area and cancellous bone), and SSI (Stress Strain Index) for the metaphyseal region and were the bone density, area, and thickness of the cortical bone, a periosteal circumference length, an endosteal circumference length, and SSI for the diaphyseal region. Software used was Rev.5.50e.

B. Result

The total bone density (mg/cm$^3$) of the metaphyseal region and the bone density of the cancellous bone were observed to be increased in the ovariectomized (OVX)/test substance-administered group as compared with in the OVX/test substance-non-administered group (OVX+Vehicle group) (Table 3). This inhibition was attributed to an increase in bone mass from the cancellous bone to the subcortical region (see FIGS. 1 and 2). On the other hand, no change was observed in the diaphyseal region (Table 4).

C. Conclusion

A decrease in bone density was observed in the OVX/test substance-non-administered group, confirming model formation.

Figure 1:
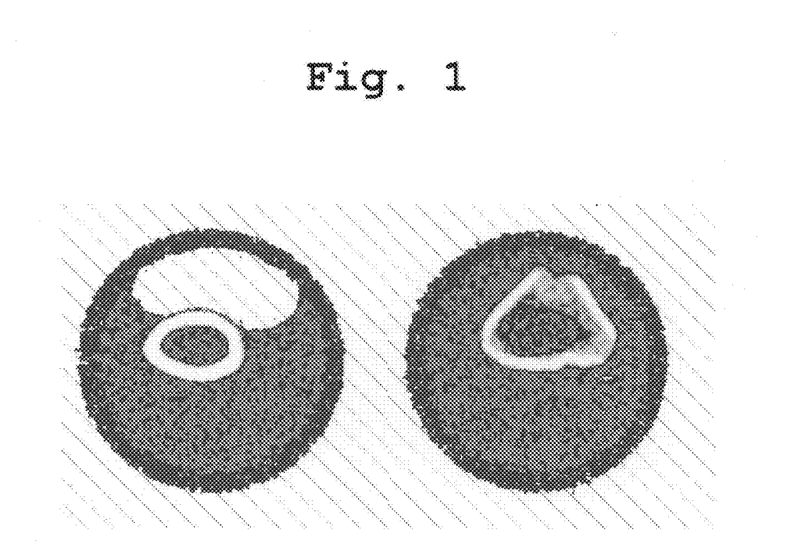
FIG. 1 shows conditions of diaphyseal region (left) and metaphyseal region (right) of ovariectomized/test substance-non-administered group.
Figure 2:
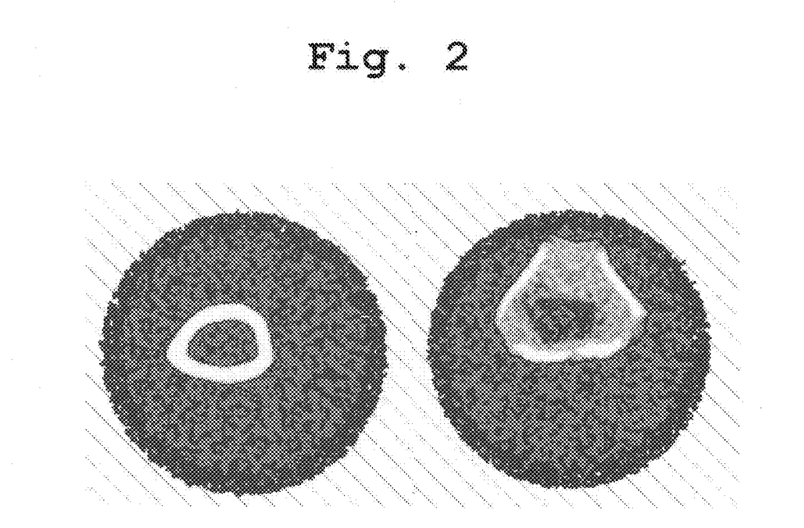
FIG. 2 shows conditions of diaphyseal region (left) and metaphyseal region (right) of ovariectomized/test substance-administered group.

The bone density of the femur metaphyseal region (both the total bone density and the bone density of the cancellous bone) was observed to increase in the test substance-administered group (FIGS. 1 and 2 and Table 3).

TABLE 3

| | | Metaphyseal region | | | | |
| --- | --- | --- | --- | --- | --- | --- |
| | | Bone density (mg/cm³) | | Area (mm²) | | |
| Group | The number of samples | Total density | Cancellous bone | Total area | Cancellous bone | SSI Polar |
| OVX + Vehicle | 3 | 473.1 ± 29.3 | 192.9 ± 24.6 | 21.69 ± 1.61 | 9.47 ± 1.52 | 9.801 ± 0.574 |
| OVX + test substance | 3 | 520.4 ± 31.7 | 253.4 ± 2.9 | 23.67 ± 1.34 | 7.44 ± 0.47 | 11.474 ± 0.346 |

TABLE 4

| | | Diaphyseal region | | | | | |
| --- | --- | --- | --- | --- | --- | --- | --- |
| Group | The number of samples | Bone density (mg/cm³) | Area (mm²) | Thickness (mm) | Periosteal circumference length (mm) | Endosteal circumference length (mm) | SSI Polar |
| OVX + Vehicle | 3 | 1265.7 ± 15.9 | 5.55 ± 0.02 | 0.551 ± 0.021 | 11.819 ± 0.333 | 8.360 ± 0.467 | 6.753 ± 0.380 |
| OVX + test substance | 3 | 1254.9 ± 14.6 | 5.50 ± 0.17 | 0.552 ± 0.038 | 11.729 ± 0.455 | 8.260 ± 0.666 | 6.877 ± 0.605 |

All publications, patents, and patent applications cited herein are incorporated herein by reference in their entirety.

INDUSTRIAL APPLICABILITY

The present invention is utilized in pharmaceutical fields such as a therapeutic drug for osteoporosis and an osteoblast activator.

The invention claimed is:

1. A compound represented by the following formula (I) or a salt thereof:

wherein X represents a halogen atom;

$R^1$ represents a hydrogen atom, substituted or unsubstituted $C_{1-6}$ alkyl group, substituted or unsubstituted $C_{2-6}$ alkenyl group, substituted or unsubstituted $C_{2-6}$ alkynyl group, substituted or unsubstituted aromatic group, substituted or unsubstituted aralkyl group, substituted or unsubstituted acyl group, substituted or unsubstituted arylsulfonyl group, substituted or unsubstituted $C_{1-6}$ alkylsulfonyl group, substituted or unsubstituted $C_{2-7}$ alkoxycarbonyl group, or hydroxyl group;

$R^2$ represents a $C_{1-21}$ alkyl group which is optionally substituted by one or more substituents selected from an aromatic group, an acyl group, a hydroxyl group, a carboxy group, and $C_{1-6}$ alkoxy group;

$R^3$, $R^5$, and $R^6$ are the same or different and represent a hydrogen atom or halogen atom;

$R^4$ represents a hydrogen atom or substituted or unsubstituted $C_{1-6}$ alkyl group; and $R^7$ represents a hydrogen atom or substituted or unsubstituted $C_{1-21}$ hydrocarbon group.

2. The compound represented by the formula (I) according to claim 1 or a salt thereof, wherein X is a bromine atom; $R^1$ is a hydrogen atom, substituted or unsubstituted $C_{1-6}$ alkyl group, substituted or unsubstituted $C_{2-6}$ alkenyl group, substituted or unsubstituted $C_{2-6}$ alkynyl group, substituted or unsubstituted aromatic group, substituted or unsubstituted aralkyl group, substituted or unsubstituted acyl group, substituted or unsubstituted arylsulfonyl group, substituted or unsubstituted $C_{1-6}$ alkylsulfonyl group, or substituted or unsubstituted $C_{2-7}$ alkoxycarbonyl group; $R^2$ is a methyl group; $R^3$, $R^5$, and $R^6$ are the same or different and are a hydrogen atom or bromine atom; $R^4$ is a methyl group; and $R^7$ is a $C_{1-6}$ alkyl group.

3. A pharmaceutical composition comprising the compound according to claim 1 or a pharmaceutically acceptable salt thereof as an active ingredient.

4. The pharmaceutical composition according to claim 3, wherein the active ingredient is in an effective amount.

5. A method for treating osteoporosis comprising administering an effective amount of the compound according to claim 1 or a pharmaceutically acceptable salt thereof to a subject in need thereof.

6. A method for activating osteoblast, said method comprising administering an effective amount of the compound according to claim 1 or a pharmaceutically acceptable salt thereof to a subject in need thereof.

* * * * *